US00PP15183P2

(12) United States Plant Patent
Olesen et al.

(10) Patent No.: US PP15,183 P2
(45) Date of Patent: Sep. 28, 2004

(54) MINIATURE ROSE PLANT NAMED 'POULULV'

(50) Latin Name: *Rosa hybrida*
Varietal Denomination: POULulv

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/738,155

(22) Filed: Dec. 16, 2003

(51) Int. Cl.[7] ..... A01H 5/00
(52) U.S. Cl. ..... Plt./116
(58) Field of Search ..... Plt./116

*Primary Examiner*—Kent Bell
*Assistant Examiner*—S B McCormick-Ewoldt

(57) ABSTRACT

A new miniature rose plant which has abundant, light peach flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULulv'.

SUMMARY OF THE INVENTION

The present invention constitutes a new and distinct variety of shrub rose plane which originated from a controlled crossing between the female parent plant, 'Mini-Poul', non patented, and the male parent plant, an unnamed seedling. The two parents were crossed and the resulting seeds were planted in a controlled environment. The new variety is named 'POULulv'.

The new rose may be distinguished from its seed parent, 'Mini-Poul', by the following combination of characteristics:

1. While the seed parent has a bud color of Red Group 55C. 'POULulv' has a bud color of Red Group 37A.
2. While the seed parent has a petal count of 40 petals under normal conditions. 'POULulv' has a petal count of 20 petals under normal conditions.

The new variety may be distinguished from its pollen parent, created by the same inventors, by the following combination of characteristics:

1. While the pollen plant has pink flowers. 'POULulv' has lightpeach flowers.
2. While the pollen plant has little to no scent. 'POULulv' has a moderate floral scent.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULulv' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULulv' was selected by the inventors as a single plant from the progeny of the hybridization in 1992.

Asexual reproduction of 'POULulv' by cuttings and traditional budding was first done by L. Pernille and Mogens N. Olesen in their nursery in Fredensborg, Denmark in 1993. This initial and other subsequent propagations conducted in controlled environments have demonstrated that the characteristics of 'POULulv' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULulv'. Specifically illustrated in the drawing:

FIG. 1.1; Open flower from above, cyme structure showing clusters of open flowers, branching, and the attachment of peduncles;

FIG. 1.2; Flower bud closed, partially open, and open;

FIG. 1.3; Flower petals, detached;

FIG. 1.4; Sepals, receptacle, and pedicel;

FIG. 1.5; Bare stem exhibiting thorns;

FIG. 1.6; Juvenile and mature leaves.

DETAILED DESCRIPTION OF THE VARIETY

The following is a description of 'POULulv', as observed in its growth in a field nursery in Jackson County Oreg. Observed plants are 3 years of age, and were grown on *Rosa multiflora* root stock. Color references are made using The Royal Horticultural Society (London, England) Colour Chart, 1995, except where common terms of color are used.

For a comparison, several physical characteristics of the rose variety 'POULtrav', a rose variety from the same inventors described and illustrated in U.S. Plant Pat. No.

13,368 and issued on Dec. 17, 2002, are compared to 'POULulv' in Chart 1.

CHART 1

| | 'POULu1v' | 'POULtrav' |
|---|---|---|
| Size of open bloom. | 35 mm. | 40 mm. |
| Petalage. | 20 petals. | 38–44 petals. |
| Color of upper surface of open bloom. | Yellow-Orange Group 14D with intonations of Yellow Group 8A at middle to basal zones. | Yellow Group 12A to Yellow-Orange Group 14B. |

Parents:

*Female seed parent.*—'Mini-Poul'.

*Male pollen parent.*—Unnamed plant.

FLOWER AND FLOWER BUD

Blooming habit: Continuous.

Flower bud:

*Size.*—Upon opening, 18 mm in length from base of receptacle to end of bud.

*Bud form.*—Broad based and pointed ovoid.

*Bud color.*—As sepals unfold, Red Group 37A. Orange Group 29B at ¼ opening.

*Sepals.*—Upper Surface: Color: Green Group 138B. Surface: Moderately pubescent. Lower Surface: Color: Yellow-Green Group 144B. Anthocyanin: Greyed-Orange Group 165A on mature sepals. Shape: Sepal apex is cirrhose. Base is flat at union with receptacle. Margins: Margins have medium to weak foliaceous appendages on three of the five sepals. Stipiate Glands: Present in average quantity. Size: 15 mm (l)×5 mm (w).

*Receptacle.*—Surface: Very glaucous. Shape: Urn-shaped. Size: 5 mm (h)×5 mm (w). Color: Yellow-Green Group 144A. Anthocyanin: Greyed-Orange Group 177C.

*Peduncle.*—Surface: Stipitate glands in medium quantity. Length: 20 to 25 mm average length. Color: Yellow-Green Group 145A. On plants grown under high light conditions, peduncle may exhibit anthocyanic intonations of Greyed-Red Group 180C.

*Borne.*—In small clusters or cymes. 5 flower buds per stem on average.

Flower bloom:

*Fragrance.*—Moderate floral scent.

*Duration.*—The blooms have a duration on the plant of approximately 10 to 12 days. Petals fall cleanly away from plant.

*Size.*—Average flower diameter is 35 mm when open.

*Form.*—Flowers develop as an open cup. Outer petals overlap slightly and reflex outward. Petals at flower center reflex somewhat inwards, creating a globular cluster.

*Shape of flower when viewed from the side.*—Upon opening upper part:Flat. Upon opening, lower part:Flat. Open flower upper part: Flat. Open flower, lower part: Flat.

*Petalage.*—25 petals under normal conditions with 4 petaloids.

Color:

*Upon opening, petals.*—Outermost petals: Outer Side: Orange Group 29C. Inner Side: Orange Group 29C with intonations of Yellow Group 8A at the middle and basal zones. Innermost petals: Outer Side: Orange Group 29C. Inner Side: Orange Group 24C with intonations of Yellow Group 8A at the middle to basal zones.

*Upon opening, basal petal spots.*—Outermost petals: Outer Side: Yellow Group 8A. Inner Side: Yellow Group 8A. Innermost petals: Outer Side: Yellow Group 8A. Inner Side: Yellow Group 8A.

*After opening, petals.*—Outermost petals: Outer Side: Orange Group 29C. Inner Side: Yellow-Orange Group 14D with intonations of Yellow Group 8A at the middle to basal zones. Innermost petals: Outer Side: Orange Group 25C. Inner Side: Yellow-Orange Group 16D with intonations of Yellow Group 8A at basal zone.

*After opening, basal petal spots.*—Outermost petals: Outer Side: Yellow Group 8A. Inner Side: Yellow Group 8A. Innermost petals: Outer Side: Yellow Group 8A. Inner Side: Yellow Group 8A.

General tonality: On open flower Yellow-Orange Group 18A to 18B with intonations of Orange-Red Group 33C to 33D. No change in the general tonality at the end of the 10th day.

Petals:

*Petal Reflex.*—Somewhat.

*Petal Margin.*—Entire with point in center of margin. Margins undulate slightly.

*Shape.*—Generally deltoid to oval. Base shape is acute. Apex is round.

*Size.*—25 mm (l)×20 mm (w).

*Thickness.*—Thin.

*Arrangement.*—Not formal.

Petaloids:

*Quantity.*—3 to 5.

*Color.*—Upper Surface: Yellow-Orange Group 16C. Lower Surface: Orange Group 25C.

Reproductive organs:

*Pistils.*—Length: 4 mm. Quantity: 37 (actual count).

*Pollen.*—None observed.

*Anthers.*—Size: 2 mm. Color: Yellow-Orange Group 15A. Quantity: 91 (actual count).

*Filaments.*—Color: Yellow Groups 13A. Length: 5 mm.

*Stigmas.*—Inferior to level relative to the height and length of the filaments and anthers. Color: Greyed-Yellow Group 162B.

*Styles.*—Color: Red-Purple Group 58A.

*Seed formation.*—Not observed.

PLANT

Plant growth: Compact, upright to bushy. When grown in a field nursery on *rosa multiflora* root stock, the average height of the plant itself is 40 to 60 cm. The spread is 40 to 50 cm.

Stems:

*Color.*—Young wood: Yellow-Green Group 144A. Older wood: Yellow-Green Group 144A.

*Surface Texture.*—Young wood: Smooth. Older wood: Smooth.

Thorns:

*Incidence.*—7 per 10 cm of stem.

*Size.*—Average length 5 mm.

*Color.*—Greyed-Red Group 181A.

*Shape.*—Concave.

Plant foliage: Normal number of leaflets on normal leaves in middle of the stem: 5 leaflets.

*Compound Leaf size.*—85 mm (l)×55 mm (w).

*Color.*—Juvenile foliage: Upper Leaf Surface: Yellow-Green Group 146A. Lower Leaf Surface: Yellow-Green Group 146A. Mature foliage: Upper Leaf Surface: Yellow-Green Group 146A. Lower Leaf Surface: Yellow-Green Group 146A. Anthocyanin intonation: Location: Central vein of the underside of leaflets.

Plants leaves and leaflets:

*Stipules.*—Size: 20 mm in length. Stipitate glands: Abundant. Color: Yellow-Green Group 146B. Anthocyanin: Located at the base of rachis.

*Petiole.*—Length: 20 mm. Color: Yellow-Green Group 144C. Underneath: Prickles observed.

*Rachis.*—Size: 40 mm. Color: Yellow-Green Group 144C. Underneath: Prickles observed. Anthocyanin: Greyed-Orange Group 177B.

*Leaflet.*—Size: 25 to 30 mm (l)×15 to 20 mm (w). Edge: Serrated. Shape: Elliptical. Apex Shape: Cuspidate. Base Shape: Round. Texture: Smooth. Arrangement: Odd pinnate. Venation: Reticulate. Glossiness: Glossy.

Disease resistance: Above average resistance to mildew, black spot, and Botrytis under normal growing conditions in Jackson County, Oreg.

Cold Hardiness: 'POULulv' has been found to be cold tolerant to USDA Cold Hardiness zone 6.

We claim:

1. A new and distinct variety of rose plant of the miniature class, substantially as herein illustrated and described as a distinct and novel rose variety due to its abundant, light peach flowers, vigorous growth, compact habit, suitability for production from softwood cuttings in pots, and durable flowers and foliage which make the variety suitable for distribution in the floral industry.

* * * * *

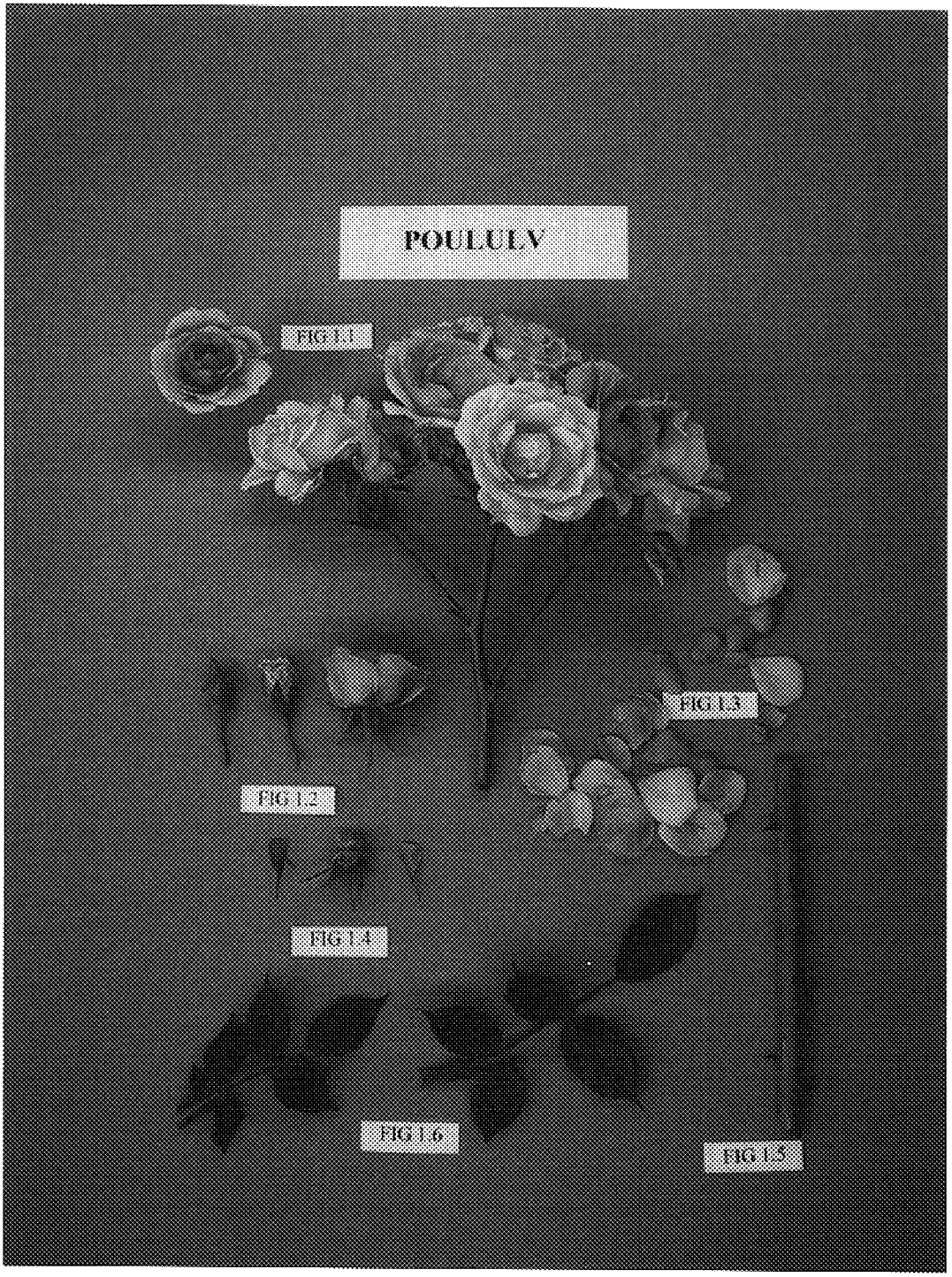
POULULV
FIG 1.1
FIG 1.2
FIG 1.3
FIG 1.4
FIG 1.5
FIG 1.6